(12) United States Patent
Park et al.

(10) Patent No.: US 11,452,605 B2
(45) Date of Patent: Sep. 27, 2022

(54) MAGNETIC ACTUATED MICROSCAFFOLD FOR MINIMALLY INVASIVE OSTEOCHONDRAL REGENERATION

(71) Applicant: Industry Foundation of Chonnam National University, Gwangju (KR)

(72) Inventors: Jongoh Park, Goyang-si (KR); Eunpyo Choi, Gwangju (KR); Chang-Sei Kim, Gwangju (KR); Gwangjun Go, Gwangju (KR); Ami Yoo, Gwangju (KR); Jin Zhen, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 446 days.

(21) Appl. No.: 15/975,311

(22) Filed: May 9, 2018

(65) Prior Publication Data

US 2019/0314156 A1    Oct. 17, 2019

(30) Foreign Application Priority Data

Apr. 16, 2018   (KR) .......................... 10-2018-0044095

(51) Int. Cl.
*A61F 2/30*   (2006.01)
*A61L 27/58*   (2006.01)
(Continued)

(52) U.S. Cl.
CPC ........ *A61F 2/30756* (2013.01); *A61K 31/728* (2013.01); *A61L 27/222* (2013.01);
(Continued)

(58) Field of Classification Search
CPC ....... A61F 2/30756; A61F 2002/30766; A61L 27/222; A61L 27/24; A61L 27/225; A61L 27/56; A61L 27/58
See application file for complete search history.

(56) References Cited

U.S. PATENT DOCUMENTS 10,668,184 B2 * 6/2020 Park .................... A61F 2/30756
2012/0021063 A1 * 1/2012 Matsumoto ............ A61L 27/60
424/602

(Continued)

FOREIGN PATENT DOCUMENTS

| JP | 200475547 A | 3/2004 |
| KR | 1020070047849 A | 5/2007 |
| KR | 10-1202839 | 11/2012 |

OTHER PUBLICATIONS

Go, G. et al., "A Magnetically Actuated Microscaffold Containing Mesenchymal Stem Cells for Articular Cartilage Repair," *Adv. Healthcare Mater.*, pp. 1-10, Wiley-VCH Verlag GmbH & Co. KGaA, Weinheim, Germany (2017).

*Primary Examiner* — Bruce E Snow

(74) *Attorney, Agent, or Firm* — Harness, Dickey & Pierce, P.L.C.

(57) ABSTRACT

Provided is a magnetically actuated microscaffold for minimal invasive osteochondral regeneration. More particularly, provided is a composition for cartilage regeneration, a microscaffold for cartilage regeneration, in which magnetic particles and cartilage regeneration cells are loaded on the surface of or within a 3-dimensional porous microstructure composed of a biodegradable polymer and having a diameter of 200-300 μm; and a microscaffold for bone regeneration, in which magnetic particles and bone regeneration cells are loaded on the surface of or within a 3-dimensional porous microstructure composed of a biodegradable polymer and having a diameter of 700-900 μm.

12 Claims, 13 Drawing Sheets

(51) Int. Cl.
*A61K 31/728* (2006.01)
*A61L 27/24* (2006.01)
*A61L 27/22* (2006.01)
*A61L 27/56* (2006.01)
*A61L 27/44* (2006.01)
*A61L 27/54* (2006.01)
*A61L 27/36* (2006.01)
*A61L 27/38* (2006.01)

(52) U.S. Cl.
CPC ............. *A61L 27/225* (2013.01); *A61L 27/24* (2013.01); *A61L 27/56* (2013.01); *A61L 27/58* (2013.01); *A61F 2002/30062* (2013.01); *A61F 2002/30766* (2013.01); *A61L 27/3654* (2013.01); *A61L 27/3817* (2013.01); *A61L 27/44* (2013.01); *A61L 27/54* (2013.01); *A61L 2400/12* (2013.01); *A61L 2400/18* (2013.01); *A61L 2430/06* (2013.01); *A61L 2430/24* (2013.01)

(56) References Cited

U.S. PATENT DOCUMENTS

2018/0028661 A1* 2/2018 Lopez ..................... A61L 27/50
2019/0314156 A1* 10/2019 Park ........................ A61L 27/56

* cited by examiner

1) Magnetically actuated microscaffold for osteocyte regeneration

2) Magnetically actuated microscffold for chodrocyte regeneration

MAGNETIC ACTUATED MICROSCAFFOLD FOR MINIMALLY INVASIVE OSTEOCHONDRAL REGENERATION

CROSS-REFERENCE TO RELATED APPLICATION

This application claims priority to Korean Patent Application No. 10-2018-0044095 filed on Apr. 16, 2018 and all the benefits accruing therefrom under 35 U.S.C. § 119, the contents of which are incorporated by reference in their entirety.

BACKGROUND

The present disclosure relates to a magnetically actuated microscaffold for osteochondral regeneration, and more particularly, to a magnetically actuated microscaffold for osteochondral regeneration which enables sequential targeting to the damaged osteochondral site.

The onset of osteoarthritis (OA) has increased as our worldwide society enters an aging society; the World Health Organization (WHO) reported that 40% of people over the age of 70 worldwide are suffering from OA. In addition, the WHO announced that incidences of knee and hip OA, as the 11th most frequent disease, have increased steadily. The OA mainly occurs in knee and hip joints and accompanies local inflammation and pain due to the loss of articular cartilage or degenerative change. In particular, because OA after its mid-term stage inflicts damage or loss to articular cartilage, it is impossible to introduce a conservative treatment, such as an anti-inflammatory analgesic, hyaluronic acid treatments, or physical therapy. Thus, the articular cartilage repair needs invasive surgery, such as microfracture techniques, autologous cell-based cartilage repair, or stem cell therapy. Recently, studies on the use of scaffolds in chondrocyte and stem cell transplants or microfracture techniques are actively ongoing. Because such scaffolds include natural or synthetic polymers having biocompatible and biodegradable properties, scaffolds implanted at the damaged articular cartilage degrade within several months. In addition, the scaffolds determine size, porosity, and biodegradation period depending on the site to be implanted. The scaffold sizes, for example, can be classified into the scale of millimeter or greater and the scale of micrometer. To implant the scaffolds having a size from several millimeters to several centimeters, a surgical operation in need of a large incision and a fixation (i.e., suture, fibrin glue) to prevent separation of the scaffolds are required. In addition, scaffolds on the comparatively large scale can lead to cell necrosis in the center thereof owing to the deficiency of nutrient and oxygen supply. In contrast, micro-scale scaffolds can solve the problem of the scaffolds having the scale of millimeter or greater and be injected through an intraarticular injection or be implanted through a minimally invasive surgery. With regard to this, Korean Patent No. 1202839 discloses "Scaffold for Articular Cartilage Regeneration and Process for Preparing the Same."

However, in the case of the related art, since there is no active actuation and thus targeting to the lesions is not achieved, the scaffolds can spread in synovial fluid after injection or implantation, so the scaffolds require a fixation to prevent separation of the scaffolds.

SUMMARY OF THE INVENTION

The present disclosure provides a magnetically actuated microscaffold for minimal invasive osteochondral regeneration which enables sequential targeting to the damaged osteochondral site to treat rapidly and efficiently. However, the object is for illustrative purpose only and the scope of the present invention is not limited thereto.

According to one aspect of the present invention, there is provided a composition for cartilage regeneration, a microscaffold for cartilage regeneration, in which magnetic particles and cartilage regeneration cells are loaded on the surface of or within a 3-dimensional porous microstructure composed of a biodegradable polymer and having a diameter of 200-300 μm; and a microscaffold for bone regeneration, in which magnetic particles and bone regeneration cells are loaded on the surface of or within a 3-dimensional porous microstructure composed of a biodegradable polymer and having a diameter of 700-900 μm.

As described above, according to an embodiment of the present invention, the effect of producing a magnetically actuated microscaffold for minimal invasive osteochondral regeneration which enables, in the same magnetic field strength, sequential targeting to the damaged osteochondral site to treat articular cartilage and subchondral bone at the same time can be realized. Of course, the scope of the present invention is not limited by these effects.

BRIEF DESCRIPTION OF THE DRAWINGS

Exemplary embodiments can be understood in more detail from the following description taken in conjunction with the accompanying drawings, in which.

DETAILED DESCRIPTION OF THE INVENTION

Figure 1:
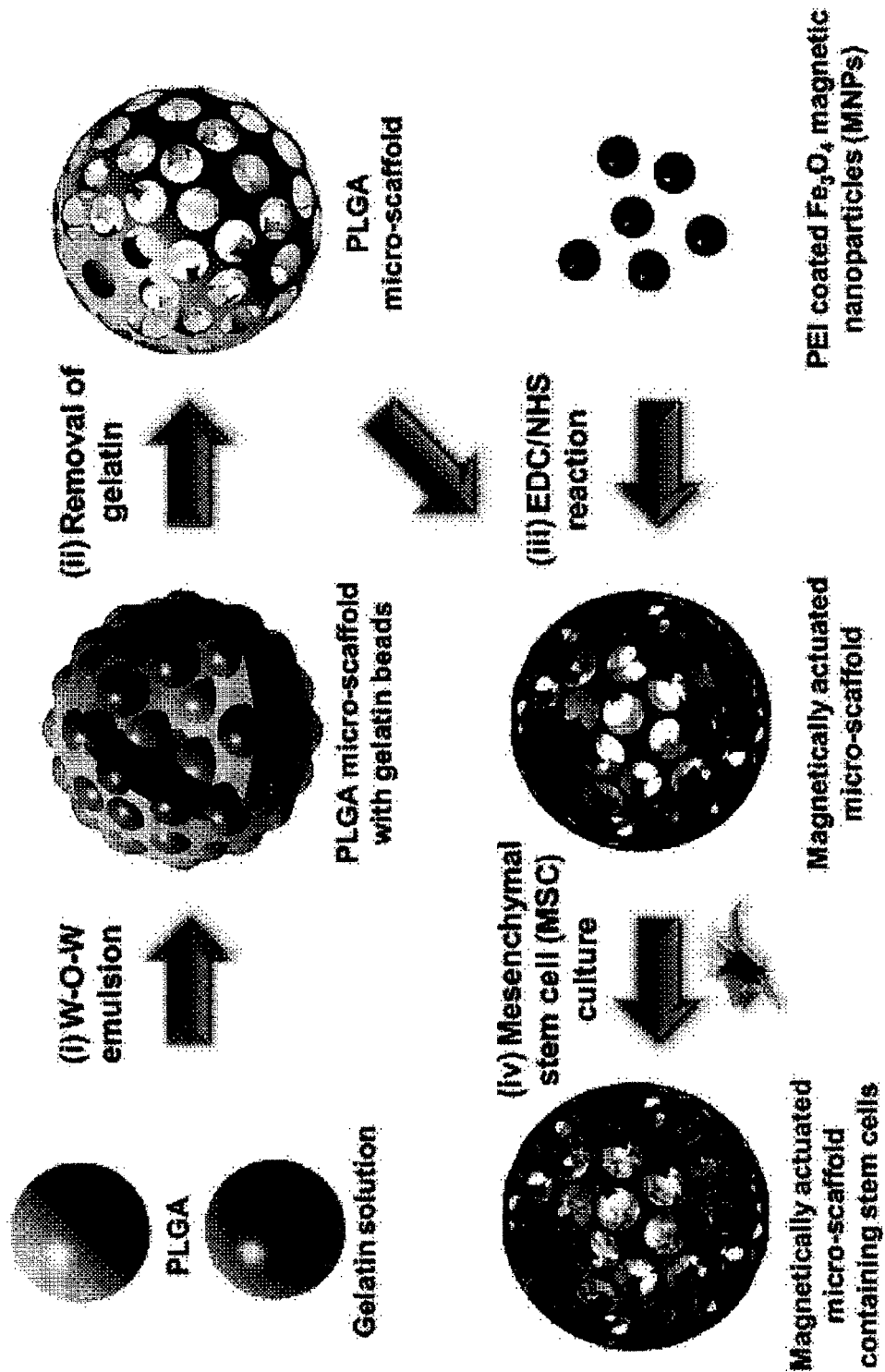
FIG. 1 is a schematic diagram illustrating a process for preparing a magnetically actuated microscaffold for minimal invasive osteochondral regeneration in accordance with an exemplary embodiment of the present disclosure, the process including (i) W-O-W emulsion, (ii) removal of gelatin, (iii) amino bond formation, preparation, and then culturing of MSCs on the magnetically actuated microscaffold, and (iv) MSC culture.

Hereinafter, specific embodiments will be described in detail with reference to the accompanying drawings.

Definitions

As used herein, the term "magnetic field" refers to a space in which lines of magnetic force are spread out, that is, a space exerted by magnetism, such as an area around electric current or a magnet, and the surface of the Earth.

As used herein, the term "osteoarthritis" is referred to as degenerative arthritis or degenerative joint disease and is a disease that accompanies progressive loss of articular cartilage in local joints and secondary changes and symptoms related thereto. The osteoarthritis is a disease that causes inflammation and pain due to progressive damages or degenerative changes of cartilage which protects a joint and leads to damage to bones, ligaments and the like, which constitute a joint, and thus the osteoarthritis shows the highest incidence among joint inflammatory diseases.

As used herein, the term "hyaline cartilage" is also referred to as a hyaline articular cartilage and is a most common cartilage tissue, most cartilage of which makes articular cartilage, epiphyseal cartilage, costal cartilage, nasal cartilage, or trachea. In addition, cartilaginous joints among bone joints, for example, the skull base of an infant linking bones with each other by hyaline cartilage, are substituted bones when the infant grows.

As used herein, the term "fibrocartilage" refers to cartilage which can be clearly distinguished from thick collagen fibers which are woven in cellular matrix present or existing between chondrocytes. Chondrocytes are sparsely dotted alone or in small groups of two or three in an abundant cellular matrix. A narrow cartilage matrix layer is formed around the chondrocytes. This cartilage exists in intervertebral disc or interpubic cartilage lamina.

DETAILED DESCRIPTION OF THE INVENTION

According to one aspect of the present invention, there is provided a composition for cartilage regeneration, which includes: a microscaffold for cartilage regeneration, in which magnetic particles and cartilage regeneration cells are loaded on the surface of or within a 3-dimensional porous microstructure composed of a biodegradable polymer and having a diameter of 200-300 μm; and a microscaffold for bone regeneration, in which magnetic particles and bone regeneration cells are loaded on the surface of or within a 3-dimensional porous microstructure composed of a biodegradable polymer and having a diameter of 700-900 μm.

In the composition for cartilage regeneration, the biodegradable polymer may be polyvinyl alcohol, polyethylene glycol, poly(lactic-co-glycolic acid) (PLGA), polylactic acid (PLA), polyglycolic acid (PGA), polyhydroxyalkanoate (PHA), polycaprolactone (PCL), or collagen, the microscaffold for cartilage regeneration may have an inner pore size of 45-115 μm, and the microscaffold for bone regeneration may have an inner pore size of 85-130 μm.

In the composition for cartilage regeneration, the magnetic particle may be magnetite or maghemite, the cartilage regeneration cells may be stem cells or chondrocytes, and the bone regeneration cells may be stem cells or osteoblasts.

In the composition for cartilage regeneration, the composition may further include a drug for cartilage regeneration, the drug for cartilage regeneration is a cell differentiation growth factor or an antibiotic, and the cell differentiation growth factor is TGF-β or BMPs.

The composition for cartilage regeneration may include a pharmaceutically acceptable carrier.

In addition to the carrier, the composition may further include a pharmaceutically acceptable adjuvant, an excipient, or a diluent.

As used herein, the term "pharmaceutically acceptable" refers to a composition which is physiologically acceptable and typically doesn't cause an allergic response such as gastrointestinal disturbance and dizziness, or a similar response when administered to humans. Examples of the carrier, excipient and diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, hydroxybenzoate, talc, magnesium stearate, and mineral oil. Additionally, fillers, anti-coagulants, lubricants, humectants, fragrances, emulsifiers, preservatives, etc., may be additionally contained. Pharmaceutically acceptable carriers and formulations suitable for the present disclosure, including those exemplified above, are described in the literature [Remington's Pharmaceutical Sciences, newest edition].

According to another aspect of the present invention, there is provided to a method of cartilage regeneration for an individual, the method including administering a therapeutically effective amount of the composition for cartilage regeneration to the individual in need of cartilage regeneration.

The method may further include transporting the composition for cartilage regeneration to an affected area using an external magnetic field.

In the method, the composition for cartilage regeneration may be administered by a joint cavity injection.

In the method, the microscaffold for cartilage regeneration and the microscaffold for bone regeneration are administered at a ratio of 1:3 to 3:1.

As used herein, the term "therapeutically effective amount" refers to a dose which results in pathologically significant ameliorating symptoms, treatment, or relieving pain.

Meanwhile, an effective dose of the composition according to an embodiment of the present disclosure may be 10 μg/kg to 100 mg/kg based on an active ingredient, a dose for each individual may be regulated depending on sex and age of the patient, progression of disease, purpose of treatment. Typically, such a dose may be regulated depending on the size of a lesion and the extent of the damage of a lesion.

Additionally, the composition according to an embodiment of the present disclosure may be formulated using a method known in the art to allow the rapid release, sustained release or delayed release of an active ingredient when the composition is administered to a mammal. Formulations include powders, granules, tablets, emulsions, syrups, aerosols, soft or hard gelatin capsules, sterile injectable solutions, and sterile powders.

The composition according to an embodiment of the present disclosure may be administered via a variety of routes including, for example, oral, parenteral (e.g., suppository, transdermal, intravenous, intraperitoneal, intramuscular, intralesional, intraarticular, intranasal, and intraspinal routes). To repair the damaged tissue, intraarticular administration is preferred, but the administration route is not limited thereto. Additionally, the composition according to an embodiment of the present disclosure may be administered using a transplant device for sustained or continuous or repeated release. The administration frequency may be once or several times per day within a desired range and the administration period is not particularly limited.

The dosage of the composition for a patient differs depending on many factors, including the patient's height, body surface area, age, a particular compound to be administered, sex, time and route of administration, general health conditions, and other drugs to be administered simultaneously. Pharmaceutically active microscaffolds for bone regeneration and/or cartilage regeneration may be present in an amount of 1 ng/body weight (kg) to 10 mg/body weight (kg) every administration; however, administration of above or below the exemplary dosage range is contemplated, particularly, considering the factors. When an administration method is continuous feeding, the dosage should be within the range of 1 μg to 10 mg unit per 1 kg of body weight per 1 min.

Generally, in the osteoarthritis treatment, since mature articular cartilage has little blood vessels and neural distribution, treatment is not focused only on the damaged site of the articular cartilage for articular cartilage regeneration in cell transplantations and microfracture techniques using scaffolds. Further, since the damaged articular cartilage has difficulty in getting nutrients, a method of regenerating the damaged site of the articular cartilage may cause formation of fibrocartilage instead of hyaline cartilage. The present inventors have made efforts to overcome this problem and finally developed a magnetically actuated microscaffold for bone and cartilage regeneration, in which a regenerative treatment can be effectively performed to treat articular cartilage and osteochondral sites including subchondral bone simultaneously with a minimal invasive method, by sequentially targeting to the damaged osteochondral site in the same magnetic field strength after injection into synovial fluid through controlling a loaded amount of magnetic particles. Because the interface between a bone and a bone is connected to each other more quickly than the interface between a cartilage and a bone or between a cartilage and a cartilage, the articular cartilage can gain sufficient nutrients from subchondral bone regenerated quickly to help the articular cartilage to be regenerated to hyaline cartilage. Most scaffolds used herein usually have a constant size and porosity, etc. for osteochondral regeneration (FIG. 1).

Hereinafter, preferred embodiments of the present disclosure will be described below in more detail with reference to the accompanying drawings.

Embodiments of the present disclosure are provided to explain this invention more completely to those skilled in the art. Further, the following embodiments can be modified in many different forms and the scope of the present invention is not limited to the following embodiments. Rather, these embodiments are provided so that this disclosure will be more thorough and complete, and will fully convey the idea of the present invention to those skilled in the art. Further, the thickness or size of each layer in figures is exaggerated for convenience and clarity of illustration.

Throughout the specification, it will be construed that when an element such as a film, a region, or a substrate is referred to as being "on", "connected to", or "coupled to" another element, it can be directly "on", "connected", "laminated" or "coupled" to the other element, or intervening elements may be present between the element and the another element. In contrast, when an element is referred to as being "directly on", "directly connected to" or "directly coupled to" another element, there are no intervening elements present between the element and the another element. Like reference numerals refer to like elements. As used herein, the term "and/or" includes any and all combinations of one or more of the associated listed items.

It is obvious that, although the terms first, second, etc. may be used herein to describe various members, components, regions, layers and/or sections, these members, components, regions, layers and/or sections should not be limited by these terms. These terms are only used to distinguish one member, component, region, layer or section from another member, component, region, layer or section. Thus, a first member, component, region, layer or section discussed below could be termed a second member, component, region, layer or section without departing from the teachings of the invention.

In addition, spatially relative terms, such as "above", "upper", "beneath", "below", "lower", and the like, may be used herein for ease of description to describe one element's relationship to another element(s) as illustrated in the figures. It will be understood that the spatially relative terms are intended to encompass different orientations of the device in use or operation in addition to the orientation depicted in the figures. For example, if the device in the figures is turned over, elements described as "above" or "upper" other elements would then be oriented "below" the other elements. Thus, the exemplary term "above" can encompass both an orientation of "above" and "below" depending on the specific direction in the figures. The device may be otherwise oriented (rotated 90 degrees or at other orientations) and the spatially relative descriptors used herein interpreted accordingly.

The terminology used herein is for the purpose of describing particular example embodiments only and is not intended to be limiting. As used herein, the singular forms "a", "an" and "the" may be intended to include the plural forms as well, unless the context clearly indicates otherwise. It will be further understood that the terms "comprises" and/or "comprising," when used in this specification, specify the presence of stated features, integers, steps, operations, members, elements, and/or groups thereof, but do not preclude the presence or addition of one or more other features, integers, steps, operations, members, elements, and/or groups thereof.

FIG. 1 is a schematic diagram illustrating a process for preparing a magnetically actuated microscaffold for minimal invasive osteochondral regeneration in accordance with an exemplary embodiment of the present disclosure. First, PLGA and gelatin solution are formed in W-O-W emulsion to disperse gelatin beads in a PLGA microscaffold (i), then gelatin is dissolved and removed using deionized water to prepare the PLGA microscaffold (ii), PEI-coated $Fe_3O_4$ magnetic nanoparticles are bonded to the surface and inner pores of the PLGA microscaffold through EDC/NHS reaction (iii), culture cells (e.g., mesenchymal stem cells (MSCs)) are attached to the magnetic nanoparticles-attached PLGA microscaffold (iv), thereby finally producing a magnetically actuated microscaffold with treatment cells attached thereto.

Figure 2:
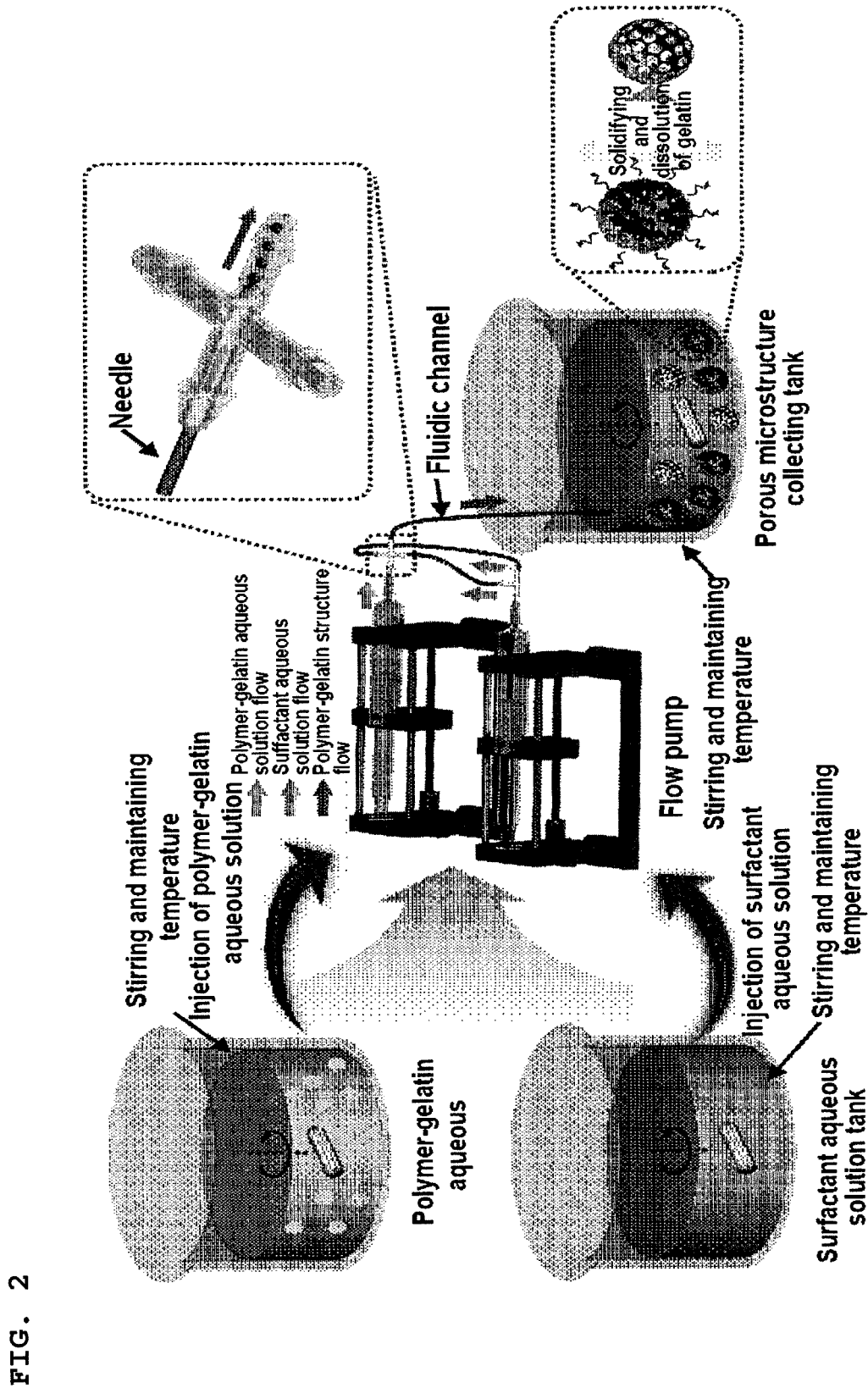
FIG. 2 is a schematic diagram illustrating a process for preparing a magnetically actuated microscaffold for minimal invasive osteochondral regeneration by regulating the size and the inner pore size of the magnetically actuated microscaffold in accordance with an exemplary embodiment of the present disclosure.

FIG. 2 is a schematic diagram illustrating a process for preparing a magnetically actuated microscaffold for minimal invasive osteochondral regeneration by regulating the size and the inner pore size of the magnetically actuated microscaffold in accordance with an exemplary embodiment of the present disclosure. As shown in FIG. 2, while polymer-gelatin aqueous solution is stirred under control of the stirring rate and temperature, surfactant is injected into separate fluidic channel by using a flow pump to be mixed with the polymer-gelatin solution through a cross-shaped connector. Thereafter, the resultant mixture is added dropwise to the porous microstructure collection tank in stirring to thereby perform solidification and dissolution of gelatin. At this time, the stirring and temperature of the porous microstructure collection tank are also regulated and maintained at a constant level.

Figure 3:
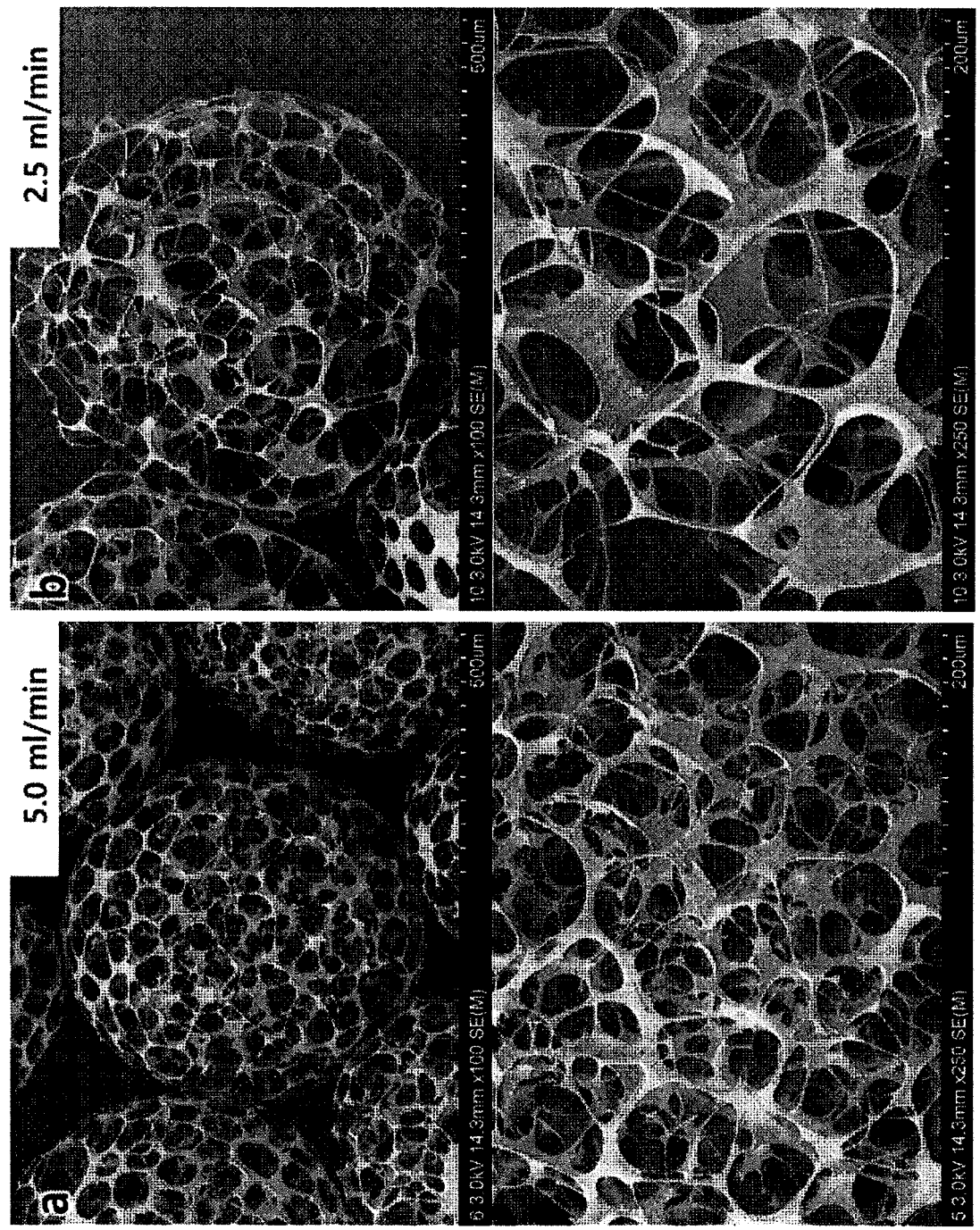
FIG. 3 is electron microscopy images showing the shapes of microscaffolds prepared by regulating the flow rate of a surfactant.

FIG. 3 is electron microscopy images showing the shapes of microscaffolds prepared by regulating the flow rate of a surfactant. The bottom of FIG. 3 is an enlarged image of the microscaffold shown in the top thereof, and shows well that the microscaffold prepared according to an embodiment of the present disclosure has a spherical shape and a porous structure in which pores are formed.

Figure 4:
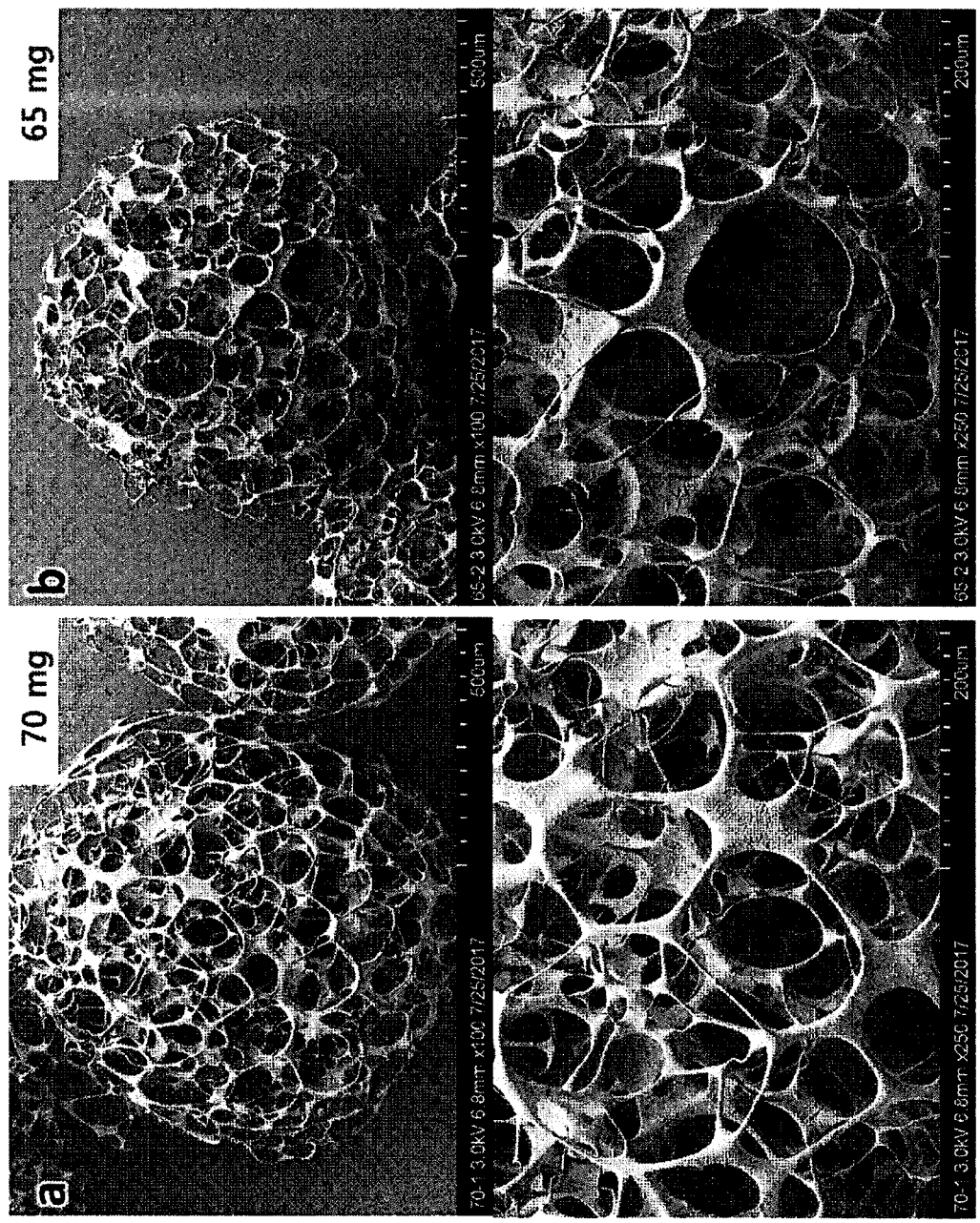
FIG. 4 is electron microscopy images showing the shapes of microscaffolds prepared by regulating the mass of a polymer.

FIG. 4 is electron microscopy images showing the shapes of microscaffolds prepared by regulating the mass of a polymer. As shown in FIG. 4, it is observed that as the mass of the polymer increases, the size of the microscaffold increases and the pores become smaller.

Figure 5:
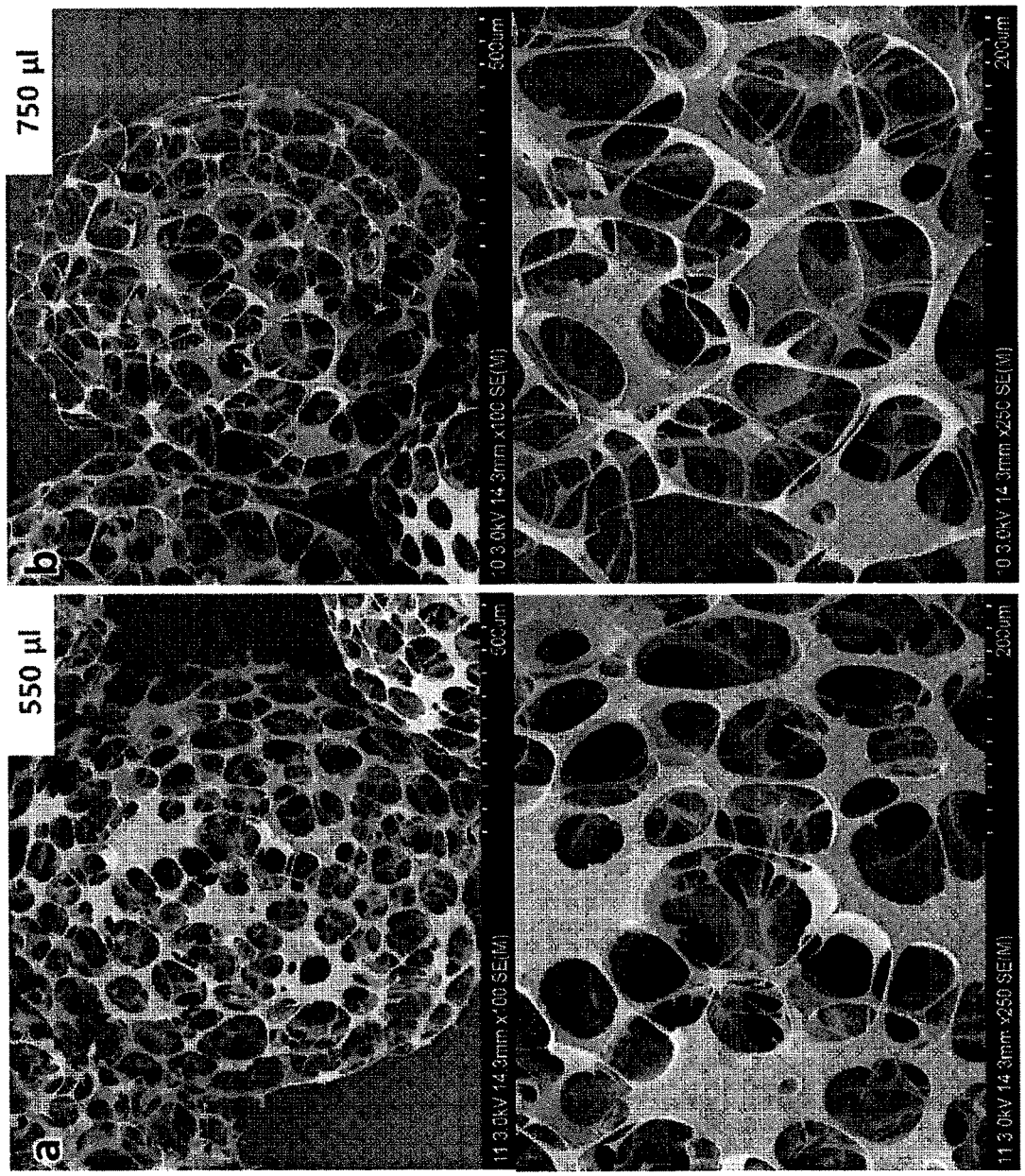
FIG. 5 is electron microscopy images showing the shapes of microscaffolds having different inner pore sizes, prepared by regulating the amount of a gelatin aqueous solution.

FIG. 5 is electron microscopy images showing the shapes of microscaffolds having different inner pore sizes, prepared by regulating the amount of a gelatin aqueous solution. As shown in FIG. 5, it is observed that when the amount of the gelatin solution is increased, the size of the scaffold and pores is increased.

Figure 6:
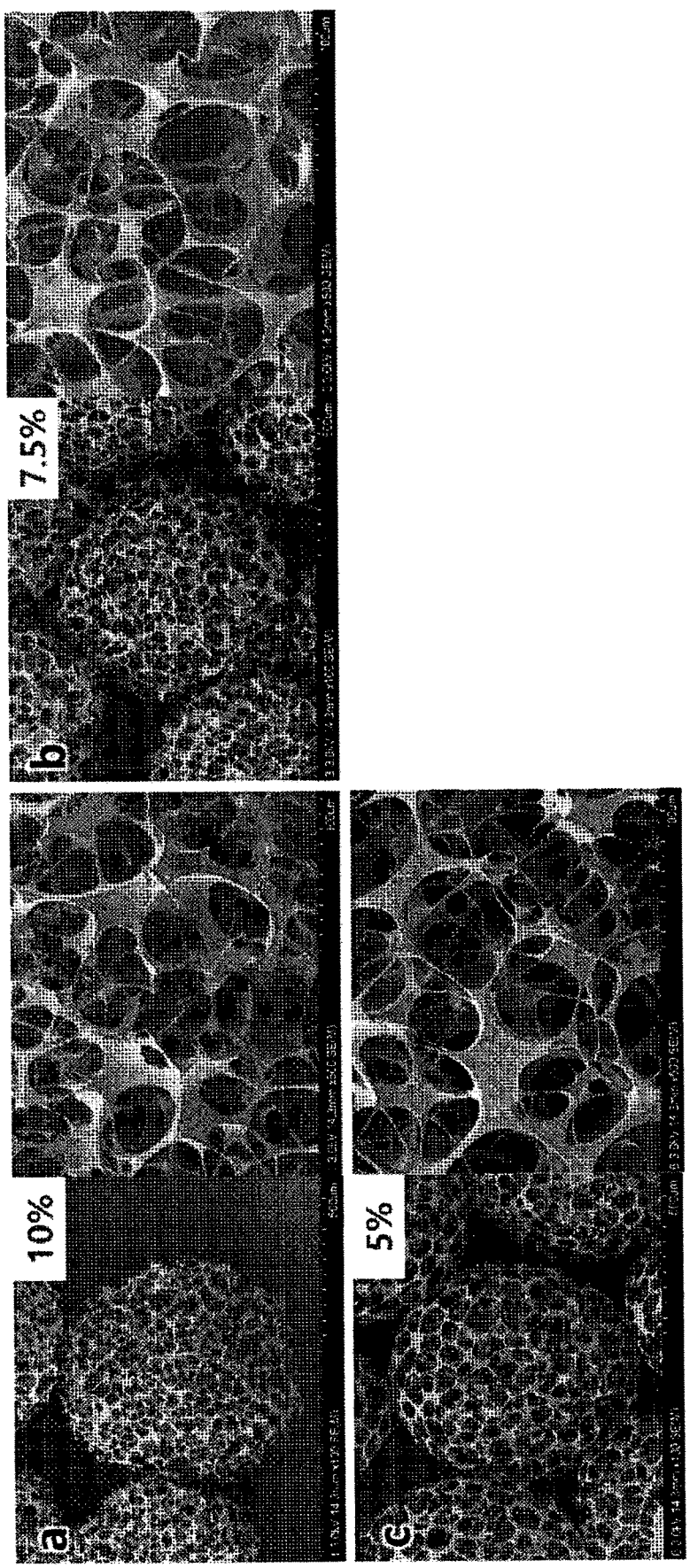
FIG. 6 is electron microscopy images showing the shapes of microscaffolds having different inner pore sizes, prepared by regulating concentration of a gelatin aqueous solution.

FIG. 6 is electron microscopy images showing the shapes of microscaffolds having different inner pore sizes, prepared by regulating the concentration of a gelatin aqueous solution. As demonstrated in FIG. 6, it is observed that when the concentration of the gelatin aqueous solution is increased, there is no significant change in the size of the microscaffold, but the size of pores is decreased.

Figure 7:
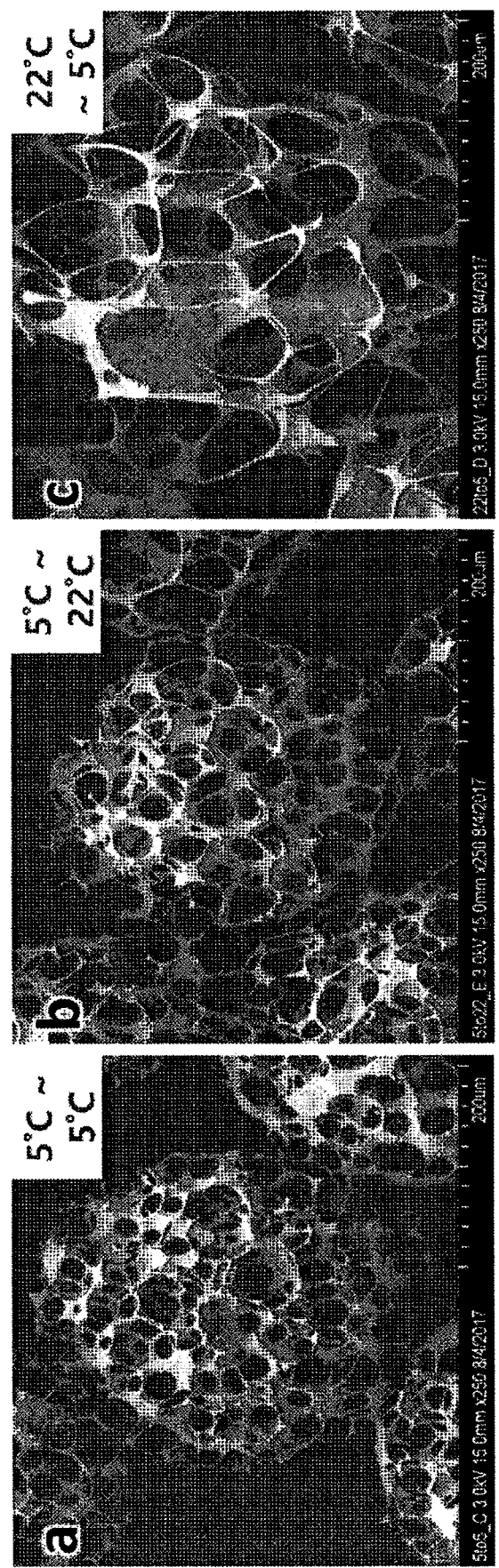
FIG. 7 is electron microscopy images showing the shapes of microscaffolds having different inner pore sizes, prepared by regulating, in solidification, the fluid temperature in a collection tank.

FIG. 7 is electron microscopy images showing the shapes of microscaffolds having different inner pore sizes, prepared by regulating, in solidification, the fluid temperature in a collection tank. As a result of regulating the fluid temperature of PLGA/gelatin aqueous solution and the temperature of the collection tank as in Table 5, the scaffold size changes little, but it is observed that when the fluid temperature is maintained at room temperature and the collection tank is cooled to 5° C., the size of pores tends to increase. In contrast, it is observed that when the fluid temperature is decreased and the temperature of the collection tank is increased, the size of pores is slightly decreased. When the fluid temperature and the collection temperature are maintained equally at 5° C., it is observed that the size of pores is the smallest.

Figure 8:
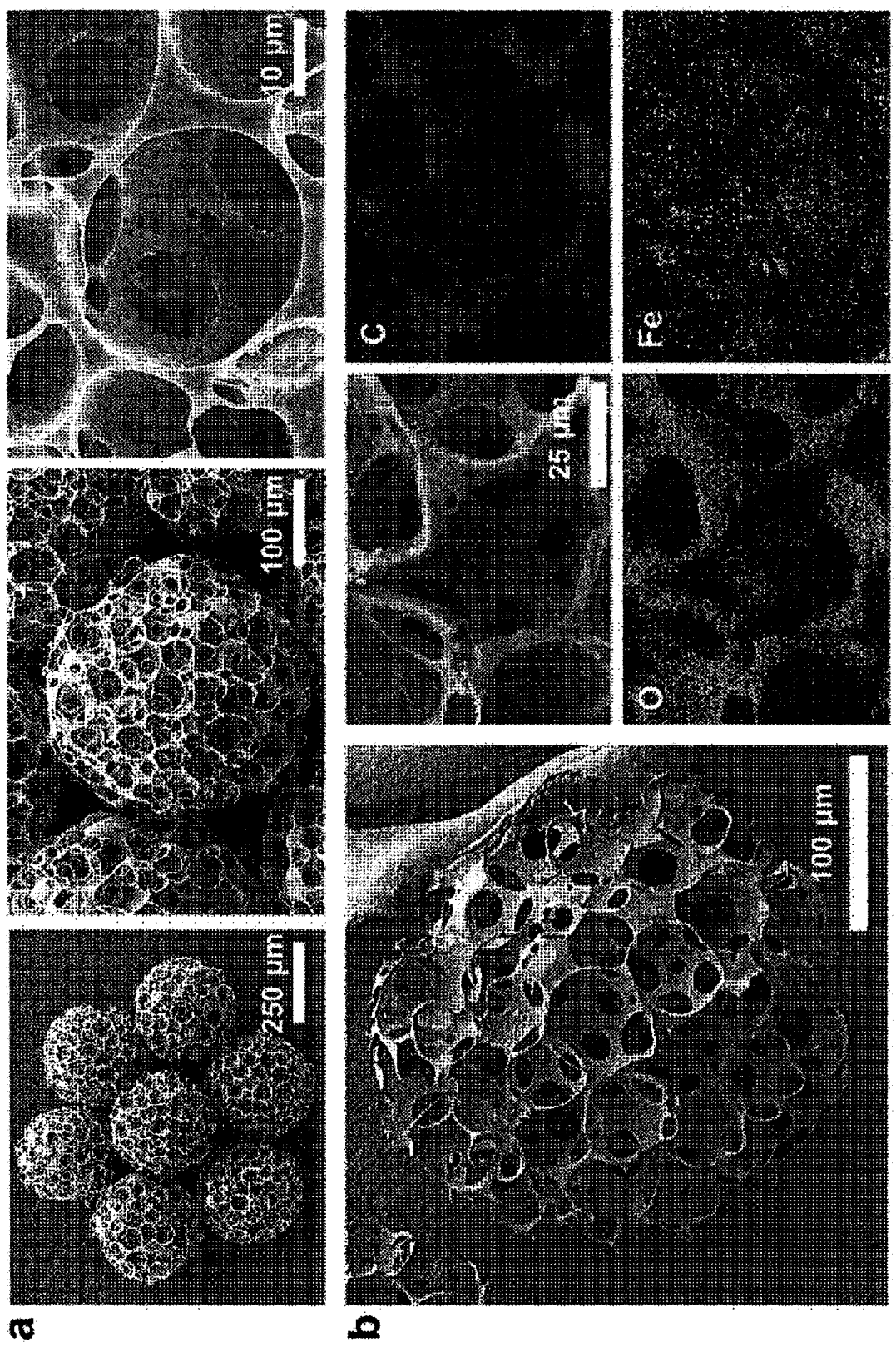
FIG. 8 is a photograph showing (a) SEM images and (b) energy dispersive X-ray spectrometry (EDX) maps for a PLGA microscaffold with amine-functionalized MNPs.

FIG. 8 is a photograph showing (a) SEM images and (b) energy dispersive X-ray spectrometry (EDX) maps for a PLGA microscaffold with amine group-functionalized MNPs. As demonstrated in FIG. 8A, the MNP-attached PLGA microscaffold has no significant change in an external diameter and a diameter of the pore, as identified in FIG. 8B, it is confirmed that the MNPs are normally attached to the surface of the microstructure.

Figure 9:
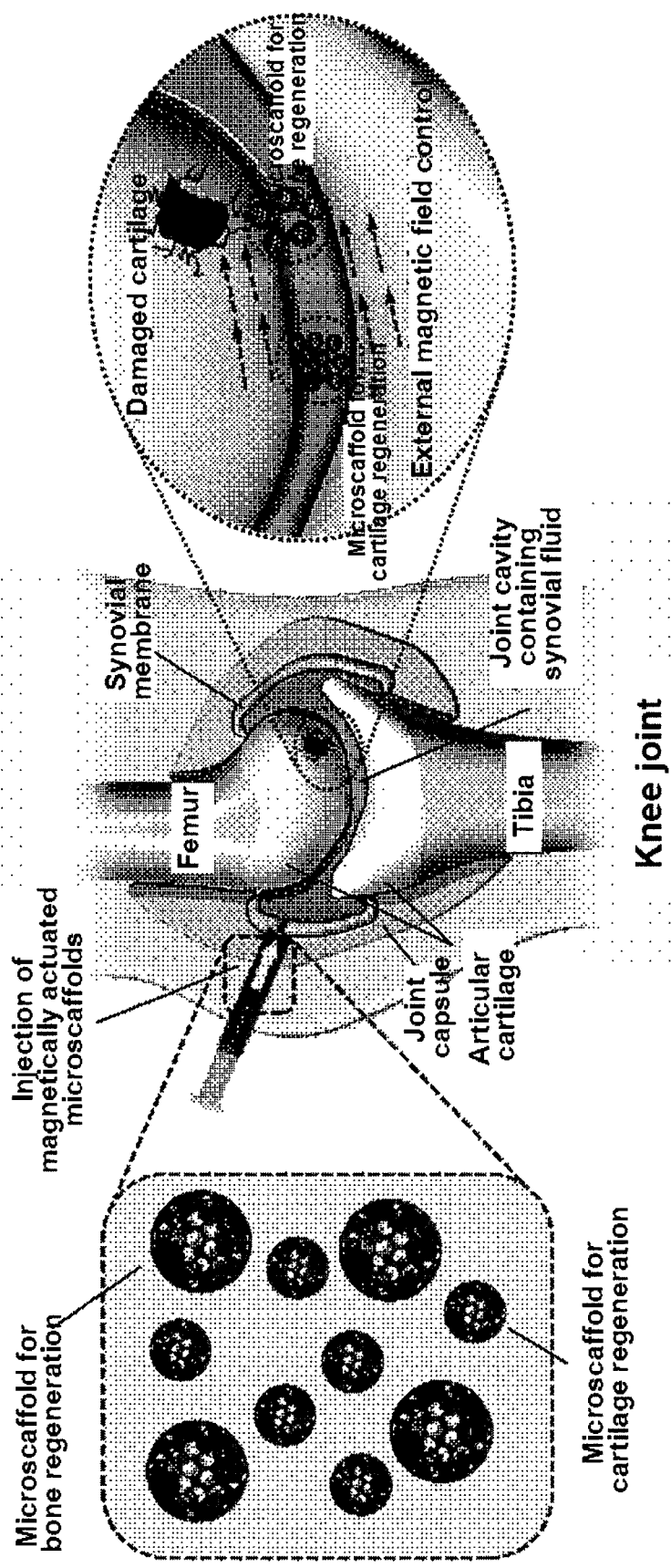
FIG. 9 is a conceptual diagram illustrating a process for osteochondral regeneration treatment using the microscaffold for bone and cartilage regeneration in accordance with an exemplary embodiment of the present disclosure.

FIG. 9 is a conceptual diagram illustrating osteochondral regeneration treatment using the magnetically actuated microscaffold for minimal invasive cartilage regeneration according to the present disclosure. As described above, the magnetically actuated microscaffold of the present disclosure is a magnetically actuated microscaffold for bone and cartilage regeneration prepared through controlling a loaded amount of magnetic particles, and is injected into synovial fluid and then sequentially targeted to the damaged osteochondral site under the same magnetic field strength, thereby effectively providing an osteochondral regenerative treatment with a minimal invasive method. In addition, as illustrated, the magnetically actuated microscaffold for minimal invasive cartilage regeneration according to the present disclosure includes a magnetically actuated microscaffold for bone regeneration and a magnetically actuated microscaffold for cartilage regeneration that are suitable for osteochondral regeneration and sequential targeting. The magnetically actuated microscaffold for bone regeneration for osteochondral regeneration is prepared to be preferentially targeted to the osteochondral bone site than the magnetically actuated microscaffold for cartilage regeneration under the same magnetic field strength. The magnetically actuated microscaffold for cartilage regeneration is injected into the intraarticular synovial fluid simultaneously, and under the same magnetic field strength applied externally, the magnetically actuated microscaffolds for bone and cartilage regeneration are sequentially targeted to the damaged bone and cartilage site due to the difference in loaded amounts of magnetic particles in the respective microscaffolds. The magnetic particles may be magnetite or maghemite, the magnetic field may be created by a soft magnet, a permanent magnet, or an electromagnet, and the permanent magnet may be a ferrite, a neodymium, an alnico, a samarium cobalt, or a rubber magnet. The magnetic force of the magnetically actuated microscaffold is determined depending on the volume of the microscaffold because the magnetic force increases in proportion to the volume. Thus, each microscaffold for cartilage and bone regeneration having a diameter of 200-300 µm and 700-900 µm has a different magnetic force, respectively, the microscaffold for bone regeneration having a larger volume has a larger magnetic force than the microscaffold for cartilage regeneration.

Figure 10:
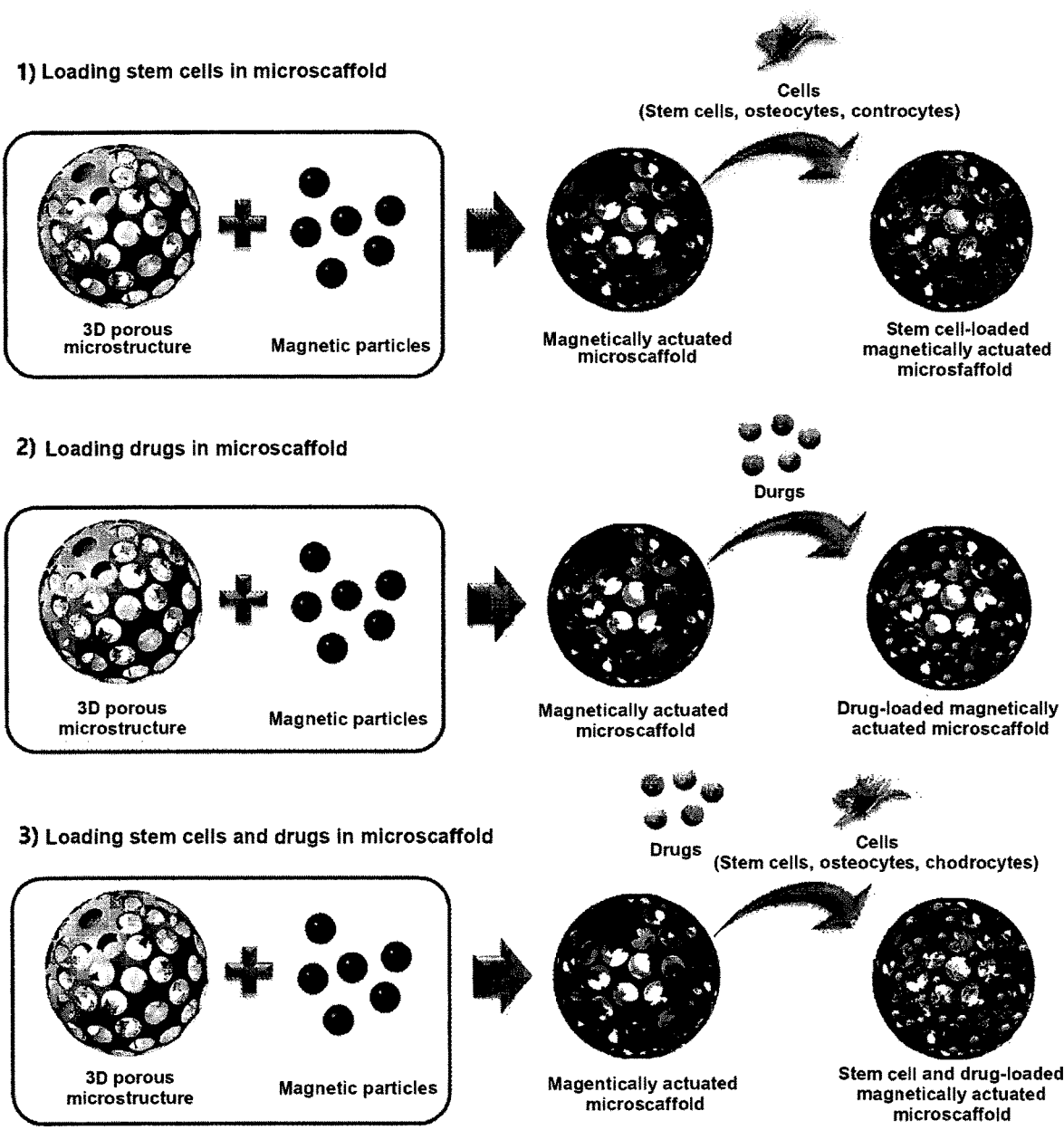
FIG. 10 is a schematic diagram illustrating a configuration of a magnetically actuated microscaffold for osteochondral regeneration in accordance with an exemplary embodiment of the present disclosure.

FIG. 10 is a schematic diagram illustrating a configuration of a magnetically actuated microscaffold for osteochondral regeneration according to the present disclosure. As illustrated, a magnetically actuated microscaffold includes magnetic particles and a 3-dimensional porous spherical microscaffold composed of biocompatible and biodegradable polymers. The magnetic particles may be present on the surface of or inside the 3-dimensional porous microscaffold, and also present on the surface of and inside the 3-dimensional porous microscaffold simultaneously. Furthermore, drug and cells for cartilage regeneration may be loaded onto the magnetically actuated microscaffold together with the magnetic particles, and drug and cells for bone regeneration may be loaded together with the magnetic particles simultaneously. The drug may be a cell differentiation growth factor (TGF-β or BMPs) or antibiotics for eliminating inflammation, the cells for cartilage regeneration may be stem cells or chondrocytes, the cells for bone regeneration may be stem cells or osteoblasts. In addition, the biodegradable polymer may be polyvinyl alcohol, polyethylene glycol, poly(lactic-co-glycolic acid) (PLGA), polylactic acid (PLA), polyglycolic acid (PGA), polyhydroxyalkanoate (PHA), polycaprolactone (PCL), or collagen.

Figure 11:
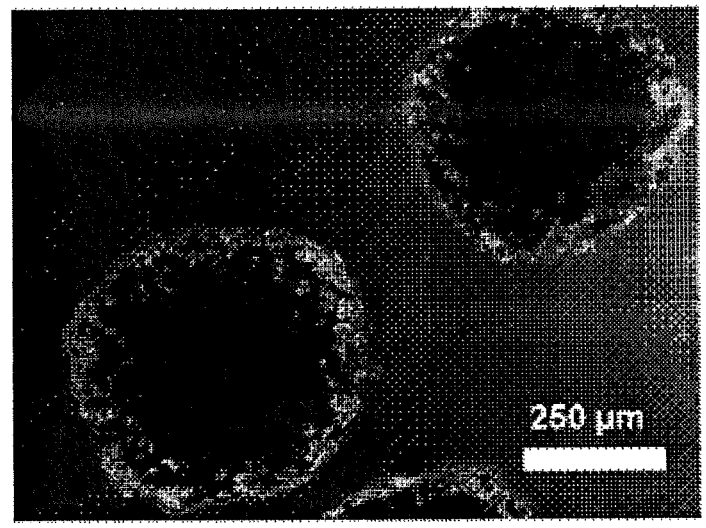
FIG. 11 is an optical image of a magnetically actuated microscaffold for bone and cartilage regeneration in accordance with an exemplary embodiment of the present disclosure.
Figure 11:
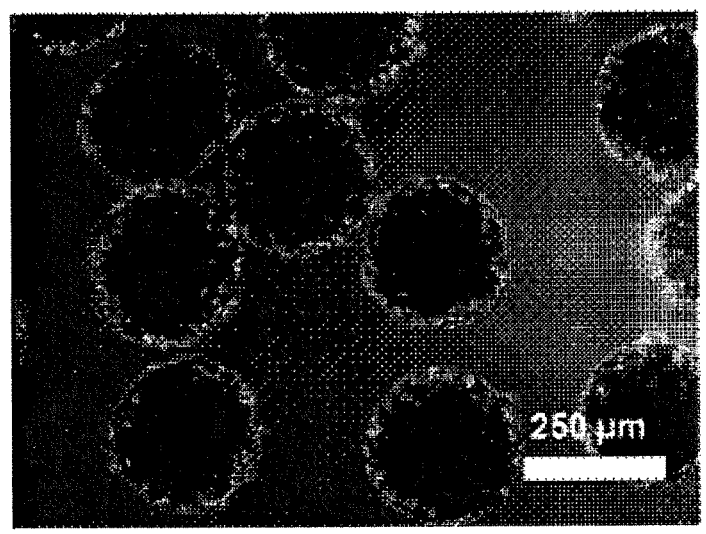

FIG. 11 is an image showing the shape of the magnetically actuated microscaffold for bone regeneration and the magnetically actuated microscaffold for cartilage regeneration that are prepared in order to regenerate bone and cartilage of the damaged osteochondral site. The magnetically actuated microscaffold for bone regeneration has a large volume (diameter of 500 μm) and surface area so as to contain more magnetic particles than the magnetically actuated microscaffold for cartilage regeneration so that the magnetically actuated microscaffold for bone regeneration may be preferentially targeted to the osteochondral bone site under the same magnetic field strength. Additionally, the magnetically actuated microscaffold for cartilage regeneration has a relatively small volume (diameter of 260 μm) and surface area so as to contain less magnetic particles than the magnetically actuated microscaffold for bone regeneration so that the magnetically actuated microscaffold for cartilage regeneration may be targeted to the osteochondral bone site after the targeting of the magnetically actuated microscaffold for bone regeneration is completed. Thus, the respective magnetically actuated microscaffolds for bone and cartilage regeneration may be sequentially targeted to the osteochondral bone site under the same magnetic field strength by the difference in a loaded amount of magnetic particles, and efficient osteochondral regenerative effect may be expected.

Figure 12:
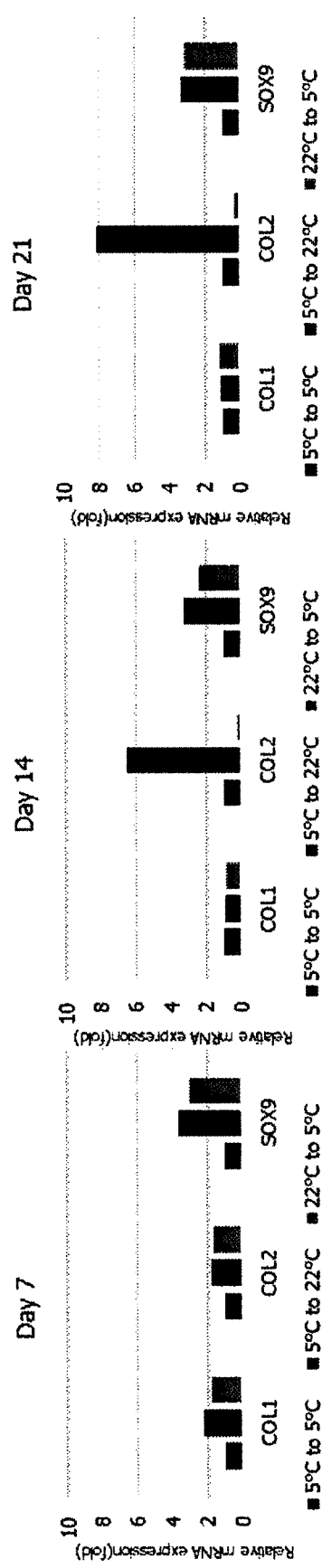
FIG. 12 is a graph showing analysis results of chondrogenic differentiation potency using the microscaffolds having different inner pore sizes, prepared by regulating, in solidification, the fluid temperature in a collection tank.

FIG. 12 is a graph showing analysis results of chondrogenic differentiation potency using the micro scaffolds having different inner pore sizes, prepared by regulating, in solidification, the fluid temperature in a collection tank. As demonstrated in FIG. 12, it is confirmed that the degree of chondrocyte differentiation varies by regulating the fluid temperature and the temperature condition of the collection tank in preparation of the PLGA microstructure. In particular, it is observed that when the fluid temperature is set to 5° C., the temperature of the collection tank is set to 22° C., and the pore size is set to meso-scale, a type II collagen expression level is the highest.

Figure 13:
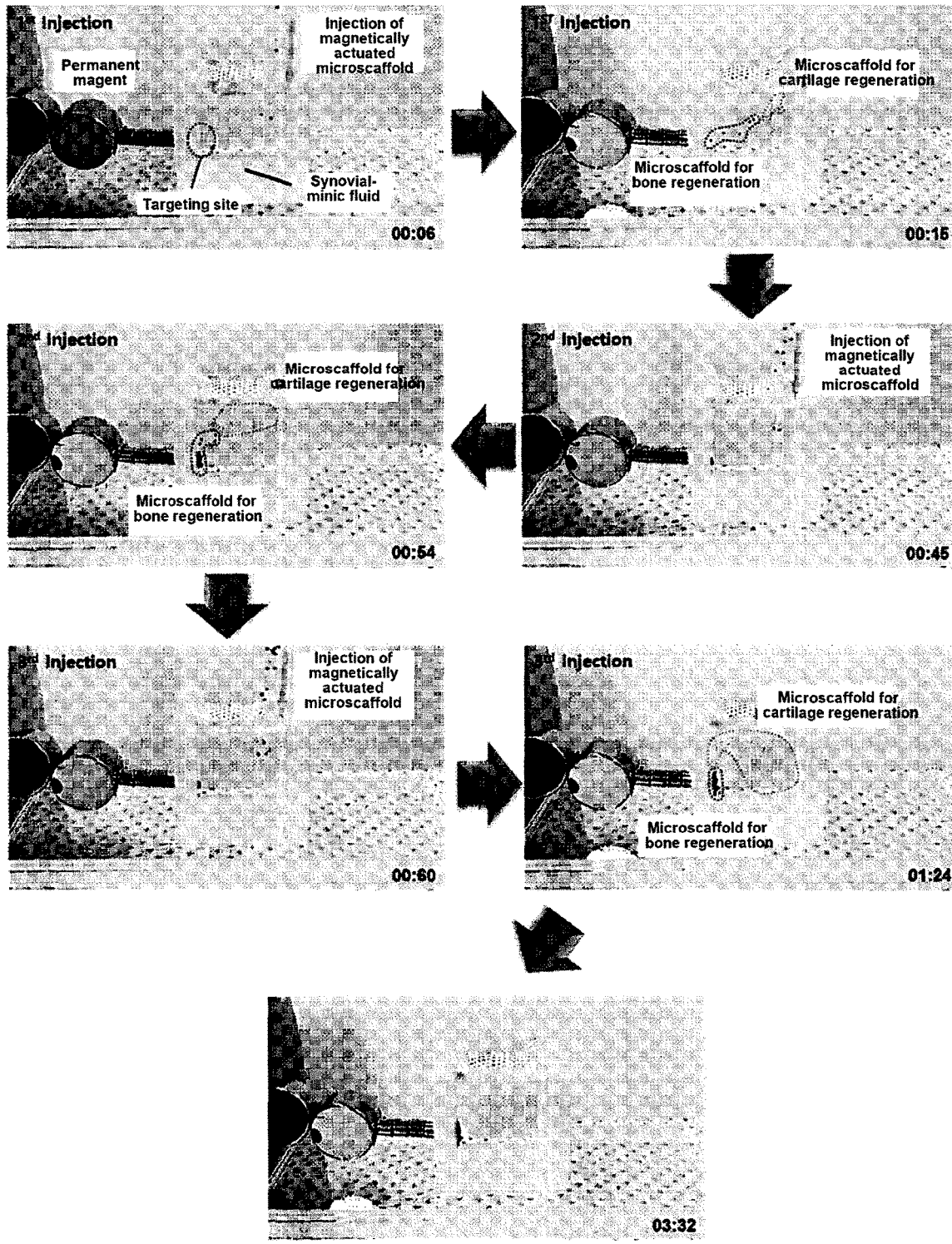
FIG. 13 is images showing a process for a targeting experiment using the magnetically actuated microscaffold for osteochondral regeneration prepared in accordance with an exemplary embodiment of the present disclosure.

FIG. 13 are images showing a process for a targeting experiment using the magnetically actuated microscaffold for osteochondral regeneration prepared in accordance with an exemplary embodiment of the present disclosure. As shown in FIG. 13, it is observed that under the same magnetic field strength, the microscaffolds for bone regeneration moves earlier to the wall of a chamber, in which the permanent magnet is placed, than the microscaffolds for cartilage regeneration. It is hereby observed that the magnetically actuated microscaffold for osteochondral regeneration according to the present disclosure is sequentially targeted to the damaged osteochondral site. This suggests that the magnetically actuated microscaffold for osteochondral regeneration according to an embodiment of the present disclosure may be effectively used for the osteochondral regenerative treatment.

Hereinafter, the present disclosure will be described in more detail with reference to Examples and Experimental Example. However, the present disclosure is not limited to these Examples and Experimental Examples described below, but may be implemented in various other forms, the following Examples and Experimental Examples are provided so that the disclosure of the present invention is complete and that those skilled in the art fully understand the scope of the invention.

EXAMPLES

Example 1: Preparation of Microscaffold

The microscaffold of the present disclosure is a magnetically actuated microscaffold composed of poly(lactic-co-glycolic acid) (PLGA) porous body and $Fe_3O_4$ magnetic nanoparticles (MNPs) attached to the surface thereof, and was prepared through an emulsion templating method and protein coupling that uses an amino bond formation (FIG. 1). In the detailed manufacturing process of the microscaffold of the present disclosure, first, the PLGA microscaffold with gelatin beads was obtained by double emulsion with a fluidic device. After the formation of W-O-W droplets, gelatin beads within the PLGA microscaffold were removed (FIG. 2).

Specifically, the fluidic device is composed of a PVC tube (1/32 in i.d.×3/32 in o.d. or 1/16 in i.d.×1/8 in o.d.), 21 G or 17 G needle, and a syringe pump, and a two-way flow channel device was fabricated by inserting a needle into the PVC tube. First, a PLGA solution and a gelatin solution was prepared for W-O emulsion, PLGA was then dissolved in 1 ml dichloromethane (DCM)/Span80 (100:1, v/v) solution, and W-O emulsion is prepared by mixing a gelatin solution in the PLGA solution at 2500 rpm for 2 min 30 sec. The W-O emulsion was poured into a 23 G or 26 G needle syringe, and then inserted into the center of the 21 G needle of the fluidic device formed via 1% PVA having a flow rate of 3 mL/min to continuously pass through the PVC tube of the fluidic device. Thereafter, the W-O-W droplets formed in the fluidic channels were introduced through the 21 G needle of the fluidic device, and were collected by deionized water placed in a 500 mL beaker of an ice bath. Subsequently, while the collected droplets were gently stirred for 6 hours, dichloromethane in the collected droplets was evaporated, the droplets were submerged in deionized water in the 500 mL beaker at 37° C. and gently stirred for 4 hours in order to remove the gelatin of droplets. Finally, after the droplets were washed three times with deionized water, the PLGA microscaffolds from which gelatin leached were stored in deionized water in a 25 mL vial.

In the above-described process, various factors of a porous scaffold, such as surface openness, interconnectivity of inner pores, porosity, and size uniformity may influence stem cell proliferation and differentiation. Thus, the size, pore size, and interconnected pore size of the PLGA microscaffold were analyzed using scanning electron microscopy (SEM) according to various experimental conditions.

Hereinafter, preferred embodiments of the present disclosure will be described below in more detail with reference to the accompanying drawings.

FIG. 3 is electron microscopy images showing the shapes of microscaffolds prepared by regulating the flow rate of a surfactant. The size of the microscaffold is determined by the flow rate of surfactant and the mass of a polymer, and it is possible to regulate the inner pore size of the microscaffold by the amount and concentration of a gelatin solution and the fluid temperature in the collection tank in solidification. For preparation of microscaffolds, a PVC tube (1/16 in i.d.×1/8 in o.d.), a 17 G needle, a 23 G needle syringe, 70 mg mass of polymer (PLGA), 750 μL of 5% gelatin aqueous solution in 1% pva (polyvinyl alcohol) were used, the fluid velocity of PLGA/gelatin aqueous solution was 0.05 mL/min, and the fluid velocity of 1% pva aqueous solution was regulated to (a) 5.0 mL/min or (b) 2.5 mL/min. As shown in the figure, it was observed that the microscaffold was prepared to have different sizes depending on the flow rate of surfactant. The size, pore size, and interconnected pore size of the prepared microscaffold are shown in Table 1 below.

TABLE 1

Comparison of Properties of Microscaffold
Depending on the Fluid Velocity

| Experimental Conditions | Scaffold Size (μm) | Pore Size (μm) | Interconnected Pore Size (μm) |
|---|---|---|---|
| 5.0 ml/min | 701.95 ± 18.46 | 114.88 ± 18.02 | 42.79 ± 14.77 |
| 2.5 ml/min | 918.38 ± 41.41 | 128.94 ± 23.01 | 67.38 ± 20.54 |

FIG. 4 is electron microscopy images showing the shapes of microscaffolds prepared by regulating the polymer mass, wherein for preparation of microscaffolds, a PVC tube (1/16 in i.d.×1/8 in o.d.), a 17 G needle, a 23 G needle syringe, 750 μL of 5% gelatin aqueous solution in 1% pva (polyvinyl alcohol) were used, the fluid velocity of PLGA/gelatin aqueous solution was 0.05 mL/min, and the fluid velocity of 1% pva aqueous solution was (b) 2.5 mL/min; however the mass of polymer (PLGA) was different from that in FIG. 3. As a result, it was observed that the microscaffold was prepared to have different sizes depending on the mass of polymer (PLGA) (a) 70 mg and (b) 65 mg. The size, pore size, and interconnected pore size of the prepared microscaffold are shown in Table 2 below.

TABLE 2

Comparison of Properties of Microscaffold
Depending on the Polymer Mass

| Experimental Conditions | Scaffold Size (μm) | Pore Size (μm) | Interconnected Pore Size (μm) |
|---|---|---|---|
| 70 mg | 918.38 ± 41.41 | 128.94 ± 23.01 | 67.38 ± 20.54 |
| 65 mg | 796.29 ± 34.79 | 129.61 ± 29.38 | 76.32 ± 20.29 |

Furthermore, the present inventors also prepared the microscaffolds by regulating the inner pore size of micro structure through changes in concentration of gelatin aqueous solution and the fluid temperature in the collection tank in solidification. FIG. 5 is electron microscopy images showing the shapes of microscaffolds having different inner pore sizes, prepared by regulating the amounts of a gelatin aqueous solution, wherein for preparation of microscaffolds, a PVC tube (1/16 in i.d.×1/8 in o.d.), a 17 G needle, a 23 G needle syringe, 70 mg mass of polymer (PLGA), (a) 550 μL or (b) 750 μL of 5% gelatin aqueous solution in 1% pva (polyvinyl alcohol) were used, the fluid velocity of PLGA/gelatin aqueous solution was 0.05 mL/min, and the fluid velocity of 1% pva aqueous solution was (b) 2.5 mL/min. As a result, it was observed that the microscaffold was prepared to have different inner pore sizes. The size, pore size, and interconnected pore size of the prepared microscaffold are shown in Table 3 below.

TABLE 3

Comparison of Properties of Microscaffold Depending
on an Amount of Gelatin Aqueous Solution

| Experimental Conditions | Scaffold Size (μm) | Pore Size (μm) | Interconnected Pore Size (μm) |
|---|---|---|---|
| 750 μL | 918.38 ± 41.41 | 128.94 ± 23.01 | 67.38 ± 20.54 |
| 550 μL | 880.64 ± 52.55 | 110.25 ± 18.61 | 58.77 ± 8.37 |

FIG. 6 is electron microscopy images showing the shapes of microscaffolds having different inner pore sizes, prepared by regulating concentration of a gelatin aqueous solution, wherein for preparation of microscaffolds, a PVC tube (1/16 in i.d.×1/8 in o.d.), a 17 G needle, a 23 G needle syringe, 70 mg mass of polymer (PLGA), 750 μL of 10% (a), 7.5% (b), or 5% (c) gelatin aqueous solution in 1% PVA (polyvinyl alcohol) were used, the fluid velocity of PLGA/gelatin aqueous solution was 0.05 mL/min, and the fluid velocity of 1% PVA aqueous solution was 5.0 mL/min. As a result, it was observed that the microscaffold was prepared to have different inner pore sizes. The size, pore size, and interconnected pore size of the prepared microscaffold are shown in Table 4 below.

TABLE 4

Comparison of Properties of Microscaffold Depending
on Concentration of Gelatin Aqueous Solution

| Experimental Conditions | Scaffold Size (μm) | Pore Size (μm) | Interconnected Pore Size (μm) |
|---|---|---|---|
| 10% | 703.17 ± 40.45 | 85.75 ± 12.71 | 36.14 ± 7.64 |
| 7.5% | 699.29 ± 28.80 | 98.97 ± 9.63 | 39.50 ± 11.53 |
| 5% | 701.95 ± 18.46 | 114.88 ± 18.02 | 42.79 ± 14.77 |

FIG. 7 is electron microscopy images showing the shapes of microscaffolds having different inner pore sizes, prepared by regulating, in solidification, the fluid temperature in the collection tank, wherein for preparation of microscaffolds, a PVC tube (1/16 in i.d.×1/8 in o.d.), a 21 G needle, a 26 G needle syringe, 70 mg mass of polymer (PLGA), 750 μL of 6% gelatin aqueous solution in 1% pva (polyvinyl alcohol) were used, the fluid velocity of PLGA/gelatin aqueous solution was 0.05 mL/min, the fluid velocity of 1% pva aqueous solution, was (b) 2.0 mL/min and the fluid temperature in the collection tank was (a) 5° C.-5° C., (b) 5° C.-22° C., and (c) 22° C.-5° C. As a result, it was observed that the microscaffold was prepared to have different inner pore sizes. The size, pore size, and cell loading amount for microscaffolds having different inner pore sizes, prepared by regulating, in solidification, the fluid temperature in the collection tank are expressed in Tables 5 and 6 below. To measure the loaded amount of stem cells in each microscaffold, $1.5 \times 10^6$ cells/mL of mesenchymal stem cells were put into the prepared microscaffolds and cultured for 48 and 72 hours, and then the cell numbers per microscaffold were measured using alamarBlue™ Cell Viability Reagent (ThermoFisher)

TABLE 5

Comparison of Properties of Microscaffold Depending on the Temperature of the Fluid and the Collection Tank

| Experimental Conditions | Scaffold Size (μm) | Pore Size (μm) | Interconnected Pore Size (μm) |
|---|---|---|---|
| 5° C.-5° C. | 306.73 ± 20.14 | 47.96 ± 9.41 | 21.79 ± 5.44 |
| 5° C.-22° C. | 281.94 ± 27.85 | 66.05 ± 7.44 | 25.31 ± 6.03 |
| 22° C.-5° C. | 290.56 ± 31.11 | 117.46 ± 19.04 | 52.69 ± 12.75 |

TABLE 6

Comparison of Attached Cell Numbers per Scaffold Depending on the Temperature of the Fluid and the Collection

| Experimental Conditions | Cell numbers after 48 hours | Cell numbers after 72 hours |
|---|---|---|
| 5° C.-5° C. | 2000 cells/scaffold | 5000 cells/scaffold |
| 5° C.-22° C. | 2500 cells/scaffold | 7000 cells/scaffold |
| 22° C.-5° C. | 4000 cells/scaffold | 7500 cells/scaffold |

Example 2: Preparation of Magnetically Actuated Microscaffolds

To allow the PLGA microscaffold prepared in Example 1 to be magnetically actuated, the present inventors chemically bonded, through protein coupling, amine group-functionalized MNPs, which are composed of a nanoscale $Fe_3O_4$ core and a PEI-coated surface, to the surface of the PLGA microscaffold (FIG. 2).

Specifically, a microscaffold was submerged in 5 mL of MES (0.1M) solution added with 1.5 mL of N-hydroxysuccinimide (NHS) and 1-ethyl-(dimethylaminopropyl) carbodiimide (EDC) at 33° C., the solution containing the microscaffold was mechanically stirred for 6 hours to activate carboxyl groups on the surface of the PLGA microscaffold. After the activation of the microscaffold surface, magnetic particles (25 mg/mL) modified in 5 mL of MES (0.1M) were added into the solution and stirred for 12 hours at 33° C. Then, the solution was filtered to remove unreactive MNPs, magnetic particles of the microscaffold fixed in the filter were collected, and the resultant solution was washed three times with deionized water.

As a result, in SEM images of the PLGA microscaffold and the MNP-attached PLGA microscaffold, the presence of the micropores and the MNPs was verified, through the EDX maps of the magnetically actuated microscaffold, the presence of PLGA and MNPs was confirmed according to C, O, and Fe signals (FIG. 8B). Compared with the PLGA microscaffold, there were no significant changes in the outer diameter and the pore diameters in the MNP-attached microscaffold because the MNPs were thinly distributed on the surface of the PLGA microscaffold.

Experimental Example 1: Differentiation Potency Experiment

The present inventors performed chondrogenic differentiation potency experiment for 3 weeks using the microscaffolds having different inner pore sizes, prepared by regulating, in solidification, the fluid temperature in a collection tank. Each week, RNAs of chondrogenic differentiation tissue were extracted using TaKaRa MiniBEST Universal RNA Extraction Kit (TAKARA), the RNAs were then synthesized to cDNA using PrimeScript™ RT Master Mix (TAKARA), and the experimental method was performed in accordance with the manufacturer's manual. By using the synthesized cDNA, the chondrogenic differentiation potencies of SOX9, which is an expression factor at the early stage of chondrogenic differentiation, and type I collagen and type II collagen, which are expression factors at the maturing stage of chondrogenic differentiation, were measured by relative polymerase chain reaction. To measure the chondrogenic differentiation potency using the microscaffolds prepared to have different inner pore sizes, the relative polymerase chain reaction was performed using three gene-specific primer pairs according to the following process. A reaction solution was prepared in a total amount of 10 μL by mixing 2 μL of 5× HOT FIREPol® EvaGreen® qPCR Mix Plus (Solis BioDyne), 1 μL of SOX9, COL1, COL primer pairs (10 pmol, Bioneer), 6 μL of RNase-Free water, and 300-500 ng of cDNA template. The polymerase chain reaction is performed in such a way that reaction is carried out at 95° C. for 15 min once; denaturation at 95° C. for 20 sec, annealing at 60° C. for 20 sec, and extension at 72° C. for 20 sec are repetitively carried out 40 times; and reaction is carried out at 95° C. for 10 sec. Thereafter, while increasing the temperature from 65° C. to 95° C. by 0.5° C. for 5 seconds, melt curve analysis was performed. The chondrogenic differentiation potency depending on the inner pore size was obtained by averaging the measured values using GAPDH gene-specific primer pairs.

As a result, in preparing the microscaffold, the differentiation potency of the microscaffold prepared under the condition where the fluid temperature in the collection tank is 5° C.-22° C. showed the highest compared to the microscaffold prepared in the condition where the fluid temperature in the collection tank is 5° C.-5° C. (FIG. 12).

Experimental Example 2: Targeting Experiment

The present inventors performed the targeting experiment so as to verify the targeting ability of the magnetically actuated microscaffolds prepared according to an embodiment of the present disclosure. Specifically, the targeting experiment was performed by using a chamber containing a glycerin (70 wt %) solution, which has a similar viscosity to the synovial fluid at room temperature, a permanent magnet which includes two cylindrical neodymium magnets (diameter 10 mm×height 20 mm) and four cylindrical neodymium magnets (diameter 2 mm×height 2 mm) with 955 kA/m of magnetization value to achieve a similar experimental environment to that of a joint. About 70 magnetically actuated microscaffolds for bone and cartilage regeneration were injected into the chamber three times at time intervals, and then the targeting ability of moving to the location where the permanent magnet was placed was observed.

As a result, as shown in FIG. 13, it was observed that the microscaffolds for bone regeneration moved earlier to the wall of the chamber in which the permanent magnet was placed than the microscaffolds for cartilage regeneration, under the same magnetic field strength. This suggests that the magnetically actuated microscaffold for osteochondral regeneration according to the present disclosure is sequentially targeted to the damaged osteochondral site to perform effectively the osteochondral regenerative treatment with a minimal invasive method.

In conclusion, the magnetically actuated microscaffold for minimal invasive osteochondral regeneration according to the present disclosure enables sequential targeting to the damaged osteochondral site through regulating a loaded amount of magnetic particles after injection into the synovial fluid. Accordingly, the micro-scale scaffolds can solve the problem of the scaffolds having the scale of millimeter or greater, and the magnetically actuated microscaffold according to the present disclosure can be used for effective osteochondral regenerative treatment by injection through an intraarticular injection or transplantation through a minimally invasive surgery.

Although the present disclosure has been described with reference to the above Examples and Experimental Examples, these are provided for illustrative purposes only, and it will be understood by those skilled in the art that various modifications and equivalent other Examples and Experimental Examples are possible without departing from the scope of the present invention. Hence, the real protective scope of the present invention shall be determined by the technical scope of the accompanying Claims.

INDUSTRIAL APPLICABILITY

The magnetically actuated microscaffold for osteochondral regeneration according to an embodiment of the present disclosure can be very effectively used in the medical field, particularly, in the orthopedics field in need of osteochondral regeneration.

What is claimed is:

1. A composition for cartilage regeneration, comprising:
   a porous microscaffold for cartilage regeneration, in which magnetic particles and cartilage regeneration cells are loaded on the surface of or within a 3-dimensional porous microstructure composed of a biodegradable polymer and having a diameter of 200-300 μm; and
   a porous microscaffold for bone regeneration, in which magnetic particles and bone regeneration cells are loaded on the surface of or within a 3-dimensional porous microstructure composed of a biodegradable polymer and having a diameter of 700-900 μm, wherein the porous microscaffold for cartilage regeneration has an inner pore size of 45-115 μm and the porous microscaffold for bone regeneration has an inner pore size of 85-130 μm.

2. The composition of claim 1, wherein the biodegradable polymer is polyvinyl alcohol, polyethylene glycol, poly(lactic-co-glycolic acid) (PLGA), polylactic acid (PLA), polyglycolic acid (PGA), polyhydroxyalkanoate (PHA), polycaprolactone (PCL), or collagen.

3. The composition of claim 1, wherein the magnetic particle is magnetite or maghemite.

4. The composition of claim 1, wherein the cartilage regeneration cells are stem cells or chondrocytes.

5. The composition of claim 1, wherein the bone regeneration cells are stem cells or osteoblasts.

6. The composition of claim 1, wherein the composition further comprises a drug for cartilage regeneration.

7. The composition of claim 6, wherein the drug for cartilage regeneration is a cell differentiation growth factor or an antibiotic.

8. The composition of claim 7, wherein the cell differentiation growth factor is TGF-β or BMPs.

9. A method of cartilage regeneration for an individual, comprising:
   administering the composition for cartilage regeneration of claim 1 to the individual in need of cartilage regeneration.

10. The method of claim 9, further comprising transporting the composition for cartilage regeneration to an affected area using an external magnetic field.

11. The method of claim 9, wherein the composition for cartilage regeneration is administered by a joint cavity injection.

12. The method of claim 9, wherein the microscaffold for cartilage regeneration and the microscaffold for bone regeneration are administered at a ratio of 1:3 to 3:1.

* * * * *